United States Patent [19]
Crosz, Jr.

[11] Patent Number: 5,916,157
[45] Date of Patent: Jun. 29, 1999

[54] ELECTRODE PATCH INCLUDING POSITION MARKER FOR PHYSICAL HEALTH CONDITION TESTS

[75] Inventor: Steven J. Crosz, Jr., Oregon, Ohio

[73] Assignee: Charles F. Schroeder, Toledo, Ohio; a part interest

[21] Appl. No.: 08/719,578

[22] Filed: Sep. 25, 1996

[51] Int. Cl.⁶ .......................................................... A61B 5/04
[52] U.S. Cl. .......................... 600/372; 600/394; 600/387
[58] Field of Search .................... 128/639, 641, 128/643, 644, 696; 607/149, 152; 600/372, 394, 387

[56] References Cited

U.S. PATENT DOCUMENTS

| | | | |
|---|---|---|---|
| 3,958,564 | 5/1976 | Langguth | 128/643 |
| 4,027,664 | 6/1977 | Heavner, Jr. et al. | 128/641 |
| 4,141,359 | 2/1979 | Jacobsen et al. | 607/64 |
| 4,576,170 | 3/1986 | Bradley et al. | 128/639 |
| 5,003,987 | 4/1991 | Grinwald | 128/639 |

Primary Examiner—Lee S. Cohen
Assistant Examiner—David M. Ruddy
Attorney, Agent, or Firm—Charles F. Schroeder

[57] ABSTRACT

An electrode patch used in tests of physical health conditions such as an electrocardiograph (ECG) electrode patch having marking means which leaves a position mark in the test site on a person being tested to permit accurate location of the site for accurate placement of electrode patches in subsequent tests in a series of test procedures on the site.

13 Claims, 2 Drawing Sheets

ELECTRODE PATCH INCLUDING POSITION MARKER FOR PHYSICAL HEALTH CONDITION TESTS

FIELD OF THE INVENTION

This invention is related to physical health condition tests such as electrocardiographic (ECG) in which an electrode patch is used having marking means which will leave a position mark in the location on a person where the patch was placed for test readings. The patch, after removal following a test, will leave a mark indicating the exact spot on the person where it was located during a test so that subsequent ECG test readings in a series can all be made in the identically same spot.

BACKGROUND

Health condition tests in which electrode patches are utilized exemplified by electrocardiographic (ECG) procedures are frequently run in a series such as four times in eight hours, or every six or eight hours, depending on the medication prescribed. In emergency rooms the tests frequently are conducted in shorter periods such as every half hour since a patient's condition in emergency conditions must be monitored closer, often just to see if the medication is performing its anticipated function. By placing the electrode patches of a test in a series in the same spots as in previous tests reliable readings can be assured. That is, the heart's electrical activity such as is picked up by a given wire lead or channel can be relied upon as having been tested each time in the same spot. Thus if there are any changes in the heart's electrical activity over a period of time in a series of tests, this can be seen when a comparison is made between two or more ECG tests in the series.

In electrocardiographic tests there are, for example, "Q", "R", "S" and "T" waves. If the patient has had or is having a heart attack or other heart problems, the graphic representation reveals the patient's heart condition in one or more of the wave forms being higher or lower than the previous readings. In other words by way of example, a change in amplitude of a wave representing a specific heart condition indicates that a deviation from the norm has or is occurring. If patches placed in a given location in a series of tests are an inch or two away from where the previous patches were located, the amplitude readings for a given wave will be artificial. If a comparison is being made between two different readings in a series, a mislocated patch entails considerable effort and time to determine that the reading is false. Such events result in considerable consternation, waste of time and possible misdiagnoses.

An ECG patch is usually made of flexible plastic material, perfectly round, about the size of a silver dollar, with an electrical connector nipple projecting from a metal button centrally located at its exposed surface for contact with an electrical wire lead of one test channel extending from the test equipment. The underside of the patch is provided with a central annular spongy plastic piece, slightly smaller in diameter than a dime, surrounding the region of the connector button which extends through the patch to permit electrical contact with the person being tested. The spongy annulus contains an electrolyte material, such as in gel form, which contacts a patient's skin for making electrical connection with the patient's skin. The remaining underside of the patch surrounding the spongy annulus has an adhesive surface which permits adherence of the patch to a patient like a protective bandage. The electrical connector button is secured to the patch such as by being riveted thereto from its exposed top surface to the underlying annular sponge material. A direct electrical connection is thereby made between the electrolyte material and the connector button. Thus when the patch is placed over a selected spot in which a test is to be conducted, the connector button makes electrical communication with the patient's skin through the electrolyte. The patch is pressed into position over the spot and held in place by the adhesive portion surrounding the sponge annulus, similar to an adhesive bandage. The patch is thus arranged to be readily removable after a test reading has been taken at the selected spot.

SUMMARY OF THE INVENTION

A marking means is provided in association with an ECG patch so that in applying a patch to a selected test location on a patient among the other spots related in an overall test of the patient, a visual mark is left behind on the patient after removal of the patch to identify the spot where the test had been conducted. One or more marks can be provided in the location of a test spot to enable subsequent patches in a series of tests to be readily placed in exactly the same spot.

The present invention is intended principally for use, but not exclusively, on short term or resting electrodes left on a patient for periods up to about 30 minutes. Such electrodes if allowed to remain for longer periods, such as 8 hours or 3 to 5 days, become painful to remove because of the long term setting of the adhesive in contact with the patient's skin. For tests over such extended periods, special long term monitoring electrodes designated for use up to 5 days and special short term monitoring electrodes designed for use up to 3 days are used.

In use of the term "dye" or "ink" in this specification it is to be understood that any of a number of marking means may be used to leave a mark on the skin of a person being tested which might also be leaving a strip of material such as a strip of tape on the site without deviating from the broad scope of the invention. It is intended by such use of either "dye" or "ink" to include any such marking material or means as will perform the marking function of the invention.

A preferred shape of mark of the invention for circular patches is an arc formed by a marking dye at the circumferential edge of the patch. Such arc-shaped mark because it is a portion of the profile of the patch can be matched quickly in applying subsequent test patches over the test spot. A mark in the form of an arc which is sufficiently long at the circumferential edge of the circular patch eg. extending for example through 30 or 45 degrees of the circle, can be readily matched by the edge of a subsequent circular electrode patch. The result is that the connector button at the center of the patch will fall directly in place over the previous test spot regardless of the rotational orientation of the patch.

Marks of subsequent patches after the first identifying mark is put in place is not always necessary since a mark is already in place. The second and third test patches, however, can be arranged to leave an added mark advanced in rotation to provide an index mark to indicate which of the series of tests it was. In this regard a mark such as a radially extending arrow pointing to the edge of the patch can be provided on the exposed surface of the patch to facilitate advancement of the arcuate mark in each subsequent test in a series as a means for counting the number of tests conducted. Further, the test patch circle can be arranged to leave an index mark corresponding to the time in 24 hours in which an ECG test was run.

In still another form of the invention the first, second and third patch, and each subsequent patch in a series can leave marks in different colors from the first to indicate which of the series of tests had already been run.

Identifying the exact spot where a test has been conducted on a patient has the feature that it will cause persons who are responsible for applying the first patch as well as each subsequent patch to be more careful as to the location of application since it can be checked for accuracy of placement by others later conducting tests in the series. Further the invention has the feature that it minimizes random placement of the patches in different spots on a patient between different care persons responsible for placing patches on a desired spot in a series of ECG tests. The test spot can always be located so that subsequent patches will be placed in exactly the same location.

In other forms of the invention, the shape of the patch can be adapted to facilitate proper relocation on a given test site. In this regard the patch might be made cross shaped or square or rectangular in shape as is available for children's ECG tests. For example, a rectangular patch can be provided with dye making means which will leave a mark at diagonally opposite corners or a square patch location can be defined by a corner "V" shaped mark so that exact placement of subsequent rectangular or square patches can be accomplished quickly and easily over the same marked location.

A marking dye such as the type used for skin marking in surgical procedures is preferred for use with the patch of the invention. Such a dye can be taken off with alcohol but will not wash off with soap and water. A dye of this type is commercially available from Devon Industries, Inc., Chatsworth, Calif. The dye can be provided in the adhesive region of the patch or at the extreme edge of the patch where it will transfer to the patient's skin upon application and where it remains upon removal of the patch.

In another form for marking the skin, the dye can be encapsulated in small capsule form so that it will burst and leave a mark upon pressure being applied during placement of the ECG test patch on the patient. In this regard a single capsule of liquid dye can be incorporated in the underside of the patch or liquid dye can be encapsulated in a multiplicity of micro-capsules which when pressed into place will burst and leave a mark. Such marks in the adhesive region of the patch will transfer to skin regions over which it has been applied and subsequently removed.

Also embodied in the concept of this invention is to provide a position marker on transcutaneous monitoring patches used in measurement of oxygen levels of neonates. In use of such patches it is important that the position of a monitoring patch on a premature infant not be duplicated because of the thin skin of premature infants. The oxygen level is measured through the pores of the infant and repeated use of patches in a preused site can be injurious. Thus providing a position marker on such patches can prevent placement of a patch in a preused site.

Other objects and structural features which are believed to be characteristic of my invention are set forth with particularity in the appended claims. My invention, however, both in organization and manner of construction, together with further objects and features thereof, may be best understood by reference to the following description taken in connection with the accompanying drawings.

DETAILED DESCRIPTION OF THE DRAWINGS

Figure 1:
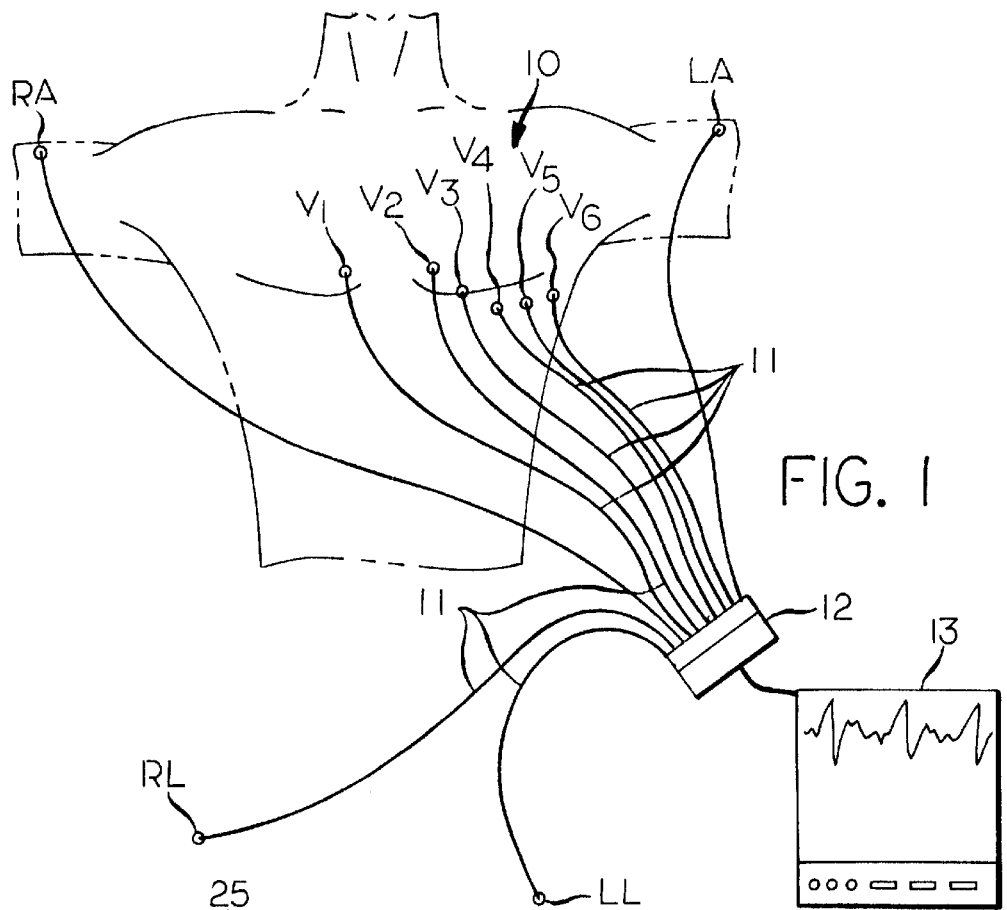
FIG. 1 is a schematic illustration of a portion of a patient's torso which electrocardiogram leads are connected from an electrocardiogram unit.

Turning to the drawings in greater detail, FIG. 1 shows a patient's torso 10 having leads 11 extending from an electrocardiographic unit 12. Each of the leads 11 extends to a selected test spot on the patient, at which an electrode patch of this invention is located. These test spots are importantly located in the chest region to provide a three-dimensional view of the heart, in addition to providing readings at the extremities of the patient's body.

Test spots V1 and V2 are located on opposite sides of the mid-region of the chest whereas test spots V3, V4, V5 and V6 are positioned to give frontal and side views of the heart action in that they approach surrounding a quadrant region of the heart. Test spots are additionally located at the right and left arm regions at points RA and LA, respectively. Further, readings are taken of the right and left leg regions at points RL and LL, respectively. The leads 11 extend between patches at each of these regions and the electrocardiogram unit at which a graphic representation is shown as on a screen 13 as well as being recorded graphically on chart paper, and optionally on computer memory.

Figure 2:
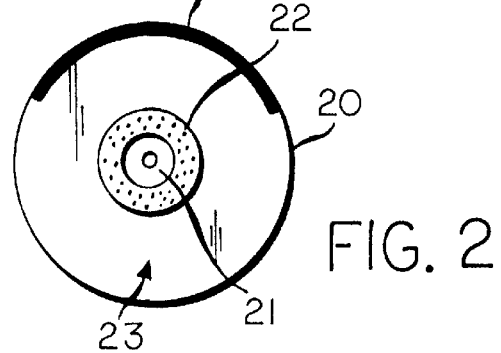
FIG. 2 is an illustration of an electrode patch arranged for electrical connection with a patient's body in one of the spots represented in FIG. 1 to which one of the leads of the electrocardiogram unit extends.
Figure 3:
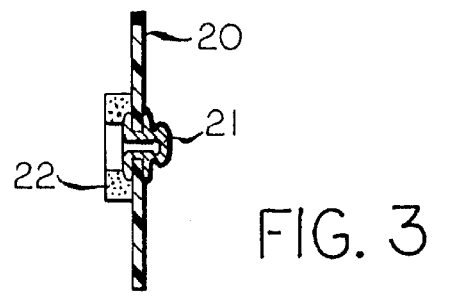
FIG. 3 is a cross-sectional, side elevational view of an electrode patch illustrated in FIG. 2.

FIG. 2 illustrates a circular electrode patch 20 of the type usually positioned at each of the test spots illustrated in FIG. 1. The patch 20 has a central electrode 21 similar to a metallic snap button riveted through the center of the non-conductive circular plastic patch which, as illustrated in FIG. 3, extends from the exterior surface of the patch to its underside. The exterior or top surface of the patch has its central electrode 21 protruding upward for ready connection of a lead 11 thereto.

The underside illustrated in FIG. 2 has the bottom of the connector 21 extending thereto and secured in connected relation to a spongy plastic- material containing a gel-like electrolyte. The connector 21 in making connection with the sponge material forms an annulus 22 which makes electrical communication with the patient's body when the patch is pressed into place over a selected test spot. The patch has a surface 23 coated with contact adhesive surrounding the spongy annulus 22. Thus when the patch is pressed into place over a selected test site an electrical lead connection is made to a patient by way of the patient's skin through the connector 21 and the underlying electrolyte containing sponge 22.

Figure 4:
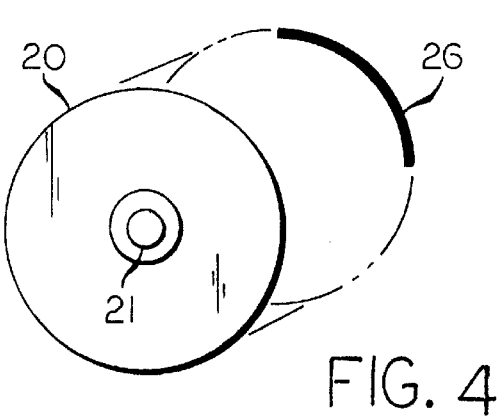
FIG. 4 is an illustration of the electrode patch represented in FIG. 2 showing how a patch can be positioned accurately in a previous test spot by being matched to a mark on a patient.

A marking region 25 at which a transferring dye is applied is provided at the circumferential edge of the patch. Upon placement of the patch 20 over a selected test spot, the dye then leaves a mark on a patient's skin corresponding in shape to the profile of the circular configuration of the patch. Although a full circular mark representing the full previous location of the patch can be provided, only a portion 25 of a full circular mark is necessary to provide a reference for exact placement of a subsequent patch in the same location. As illustrated in FIGS. 2 and 4 the portion 25 need only extend a distance adequate to provide a reference 26 which can be readily matched by a subsequent patch for accurate placement in the desired test spot. In this regard an arc 26 of about 30 to 45 degrees is found adequate to assure exact location of a patch in the same location as the previous marking patch.

Figure 5:
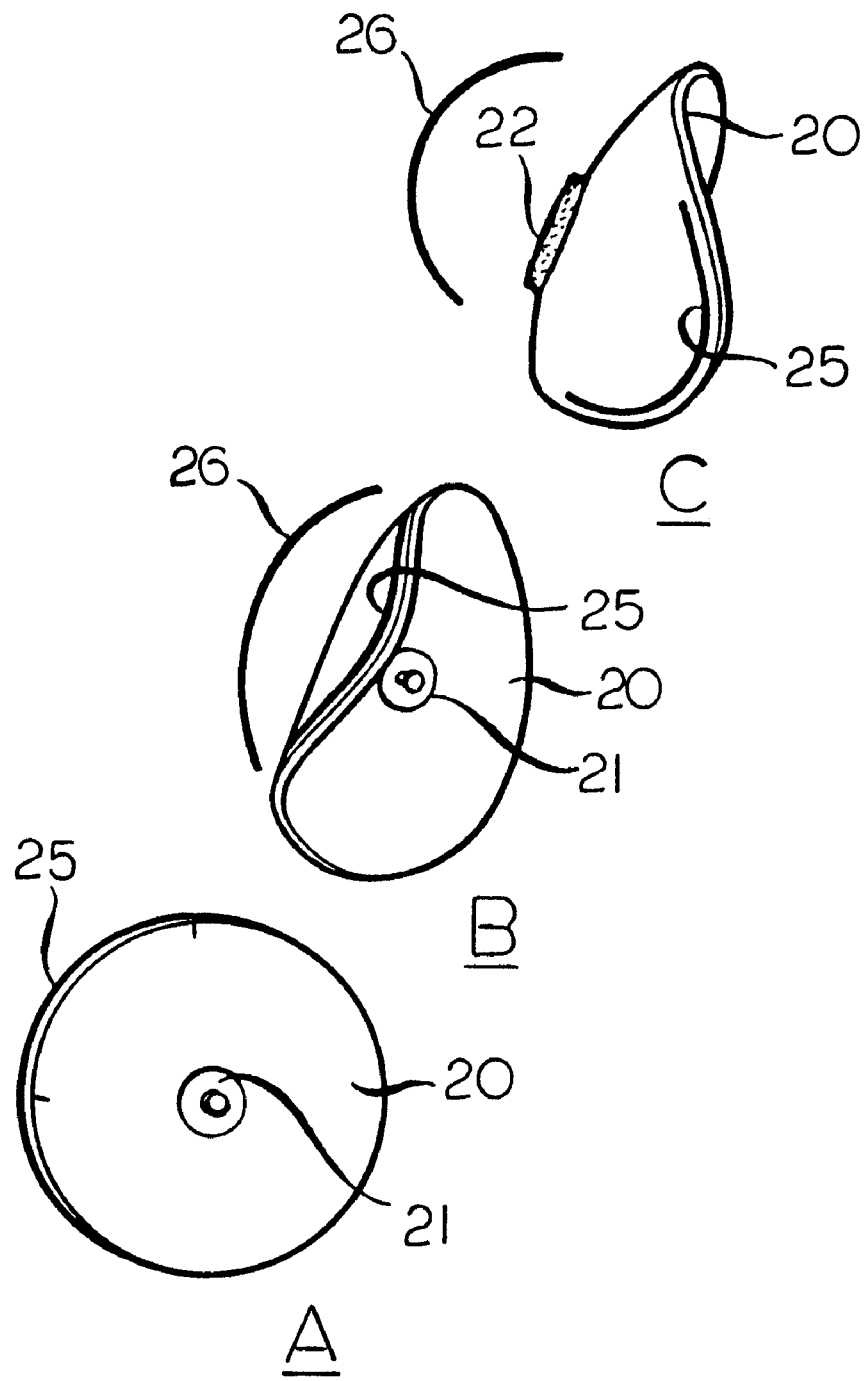
FIG. 5 is an illustration of the electrode patch represented in FIG. 2 illustrating progressively how the patch is positioned in step A in a test site and then pealed off in steps B and C to leave a location mark.

FIG. 5 shows more clearly how the patch 20 with the marking region 25 is in a test site. The top view in FIG. 5A shows the patch with its connecting terminal 21 in a test site. FIG. 5B illustrates how the patch 20 is peeled back a portion of the way in its removal. The marking region 25 having the dye material at the circumferential edge of the patch leaves a mark 26 in the form of an arc on the patient to permit ready positioning of a subsequent patch in exactly the same location. FIG. 5C illustrates still further the peeling back of the patch 20 with the full marking region 25 on the underside of the patch exposed as well as the sponge electrolyte material 22 surrounding the underside of the electrode button 21.

Since the first arcuate mark in a series in a given test spot will provide a reference for each subsequent test patch used in the selected spot in a series of tests, each subsequent patch placed over the spot can be arranged to leave a reference index mark to indicate the number of tests in a series which have been conducted at the selected spot. Such a mark might be a dot or a dash left behind each time a test is conducted so that after the first test in a series, the number of dots or dashes can be counted to indicate the total number of tests already conducted. As one option such subsequent test marks can be located radially inward from the outer edge of the patch to avoid interference with the primary arcuate mark. As indicated subsequent marks after the first can also be in different assigned colors to indicate quickly the number of tests in a series which were previously conducted. Another feature of such an arrangement is that it reveals whether any of a series of tests to be conducted were missed.

Figure 6:
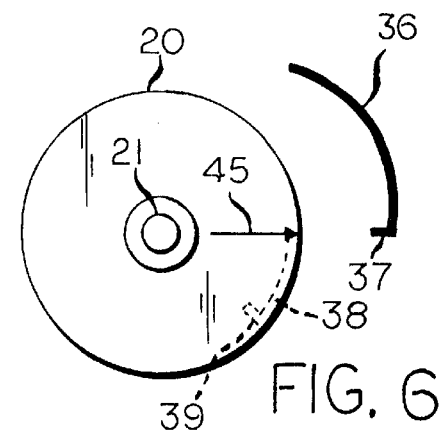
FIG. 6 is a top view of the type of electrode represented in FIG. 2 illustrating how a patch can be provided with an index mark to facilitate rotational positioning of the patch in a previous test spot to leave a reference mark for counting the number of tests conducted in a series.

FIG. 6 illustrates another arrangement of the invention in which an electrocardiogram electrode patch 20 is arranged to leave a profile reference mark 36 as in the arrangement of FIG. 4 but in addition leaves a radially extending index mark 37 at one end of the arc to which an arrow 45 marked on the exposed upper surface of the patch 20 can be matched. Such mark of the arrow 45 with the index mark 37 advances the patch rotationally a step beyond the patch of the previous test position, thereby providing an added mark 36 and index mark 37 which can be later counted to indicate the number of tests already conducted. The arrow mark 45 on the exposed upper surface points radially outward to the edge of the patch just above the end of a marking region 38 with an index marker 39 for leaving an arc-shaped mark 36 so that upon placement of the patch in the test site, matching of the arrow 45 with the index mark 37 will result in rotational advancement and extension of the arc 36 with an additional arc section as well as another index mark 37. Thus the arc extensions 36 and index marks 37 can be counted to indicate the number of ECG tests already conducted in a prescribed series.

The concept of the invention is applicable as well to providing site marks on patients when suction-cup electrodes are used in health measurement tests. In such case, a transferable marking dye can be applied to the bottom of each suction-cup prior to being secured to a test site on the patient. A mark is thereby left on the test site upon removal of a respective suction-cup electrode to identify the location of the site for later tests. In this regard it is to be understood that in use of the terminology "electrode patches" that suction-cup electrodes are also meant to be included.

In view of the foregoing it will be understood that many variations of the arrangement of my invention can be provided within the broad scope of principles embodied therein. Thus while particular preferred embodiments of my invention have been shown and described, it is intended by the appended claims to cover all such modifications which fall within the true spirit and scope of the invention.

I claim:

1. An electrocardiogram (ECG) electrode patch for use in electrocardiographic testing of a person's heart condition, said electrode patch including means for holding said patch over a selected test location on the body of a subject to be tested, said electrode patch including means for marking said test location on the subject's body where the patch is held during test, said means for marking the test location being effective to leave a location mark for subsequent similar tests in said selected location upon removal of said patch following the test, said electrode patch being circular in configuration, said means for marking comprising a dye on the circumferential edge of said patch which leaves an arc-shaped mark in said test location corresponding to the curvature of the edge of said patch, said arc-shaped mark being sufficiently long to permit matching of the edge of a circular patch of a subsequent test in exactly the same said test location, said arc-shaped mark having an index mark associated therewith to indicate the number of the test conducted by said patch in a planned series of tests.

2. A method of conducting a series of electrocardiogram (ECG) tests in testing a subject for heart conditions comprising, applying and securing an ECG electrode patch in a selected test location on the body of a subject to be tested, leaving a location mark from said patch in said selected location after removal of a first said patch following a test, and placing each successively applied patch in subsequent tests in said series in the same location in matched relation to said mark.

3. A method as set forth in claim 2 including matching another ECG patch to said location mark in a subsequent test conducted in said series to assure placement of said other patch in the same test location as said first patch.

4. A method of conducting a series of electrocardiogram (ECG) tests as set forth in claim 2 in which the electrode patches used are circular and the mark left in said selected location is an arc imprinted on the site by a dye conforming in shape and provided at the edge of at least said first circular patch.

5. A method of conducting a series of electrocardiogram (ECG) tests as set forth in claim 4 including providing an index mark in association with said arc-shaped location mark for rotationally indexing of subsequent patches to indicate the number of tests conducted in a series.

6. A method of conducting a series of electrocardiogram (ECG) tests as set forth in claim 5 including providing a reference mark on the exposed surface of said patch to facilitate matching said reference mark to a preceding index mark on said subject for rotational indexing of said patch in relation to the rotational position of preceding patches in a series of tests conducted.

7. An electrode patch for test measuring the physical condition of a patient, said electrode patch including means for holding said patch over a selected test site on the body of a subject to be tested, said electrode patch including means for marking said test site on the subject's body where the patch is held during test, said means for marking the test site being effective to leave a location mark in said selected site after removal of said patch following a test, said electrode patch comprising one of a series of individual electrode patches for testing the physical condition of said patient in said selected test location on the body of the patient, whereby each of said series of electrode patches in turn can be matched to said location mark to place each patch in said series in identically the same test location, each said patch in said series being arranged to leave a mark in said test site separate from previous marks for indication of the number of tests completed.

8. A series of electrode patches as set forth in claim 7 in which each patch in said series is arranged to leave a mark of different color from the mark of the preceding patch in said series.

9. An electrode patch as set forth in claim 7 in which said marking means is a dye transferrable to the skin of said subject during testing.

10. An electrode patch as set forth in claim 9 in which said marking dye transferred to the subject is not water washable but is removable with alcohol.

11. An electrode patch as set forth in claim 7 in which said means for holding said patch over said test site is in the form of a suction-cup to which marking means is applied.

12. A method of measuring a physical condition of a patient in a selected test site with a series of electrode patches to be used in said selected test site, holding each of said series of patches over said selected test site each in turn for a predetermined test period, leaving a location mark at said test site with at least the first patch of said series, and placing each patch of said series after said first patch in matched relation with said location mark to thereby place each patch of said series in identically the same test site during said series of tests.

13. A method as set forth in claim 12 including transferring from each patch after said first patch a reference mark which indicates that the test with each said respective patch in said series had been conducted.

* * * * *